United States Patent [19]

Grinnan et al.

[11] Patent Number: 4,612,367

[45] Date of Patent: Sep. 16, 1986

[54] PROCESS FOR PURIFYING GROWTH HORMONE-LIKE MATERIALS

[75] Inventors: Edward L. Grinnan, Carmel; Edward E. Logsdon, Indianapolis, both of Ind.

[73] Assignee: Eli Lilly and Company, Indianapolis, Ind.

[21] Appl. No.: 720,642

[22] Filed: Apr. 8, 1985

[51] Int. Cl.$^4$ .......................... C07K 3/12; C07K 3/18; C07K 3/20

[52] U.S. Cl. ................................. 530/399; 530/344; 530/413; 530/415; 530/417; 530/809; 530/825; 530/808; 435/172.3; 435/240; 435/241

[58] Field of Search .................... 260/112 R, 112.5 R; 435/172.3, 240, 241, 849

[56] References Cited

U.S. PATENT DOCUMENTS

| | | | |
|---|---|---|---|
| 3,649,456 | 3/1972 | de Bonneville et al. | |
| 4,115,375 | 9/1978 | Pedersen | 260/112 R |
| 4,332,717 | 6/1982 | Kanaoka et al. | 260/112 R |
| 4,371,462 | 2/1983 | Hecht | 260/112 R |
| 4,426,323 | 1/1984 | Jain | 260/112 R |

OTHER PUBLICATIONS

Rohm and Haas bulletin–Amberlite Polymeric Adsorbents, (undated).
Pietrzyk et al., *Anal. Chem.*, 53, 1822–1828 (1981).
Pietrzyk et al., *J. Liq. Chromatog.*, 5, 443–461 (1982).

*Primary Examiner*—Howard E. Schain
*Attorney, Agent, or Firm*—William C. Martens; Leroy Whitaker

[57] ABSTRACT

This specification describes a process for separating impurities from an impure mixture containing growth hormone-like material with substantially complete recovery of said growth hormone-like material, which comprises:

(1) applying said mixture to a reverse phase macroporous acrylate ester copolymer resin support at a pH of from about 7 to about 9; and (2) eluting said growth hormone-like material from said support with an aqueous eluant having a pH of from about 7 to about 9 and containing from about 20% to about 80% by volume of an organic diluent selected from the group consisting of acetone, acetonitrile, and a combination of acetone and acetonitrile.

17 Claims, No Drawings

PROCESS FOR PURIFYING GROWTH HORMONE-LIKE MATERIALS

BACKGROUND OF THE INVENTION

Proteins are biopolymers which are dependent upon structural stability to enact their specified function. Since a small change in solvent composition, pH, temperature, and salt concentration can often exert a significant and occasionally irreversible change in protein conformation, chromatographic protein purification has ideally been performed using resins exhibiting minimal non-specific, denaturing interactions. Classically, such resins have been extremely hydrophilic, having a water content often exceeding 80%. As a result of their hydrophilic nature, the resultant chromatographic resin particles are most susceptible to collapse, even under modest back-pressure. In addition, any non-specific adsorption can be difficult to displace due to an inability to effectively wash these hydrophilic resins with organic solvents. Consequently, one is confronted with a problem in the initial step of preparative purification of proteins from heterogeneous natural sources. The more desirable supports, due to their hydrophilic nature, are inappropriate for rapid throughput of viscous, sludge-laden, natural product mixtures. As a result, it has been necessary to use, at considerable additional expense, non-chromatographic methods for initial purification.

Amberlite ® XAD resins are polymeric macroreticular adsorbents, commercially produced by the Rohm and Haas Company. These resins have been designed for the separation of compounds based upon the varied affinity of the latter for a polymeric hydrophobic surface. Since XAD-type resins (1) have a large particle size (20–50 mesh) and (2) are extremely hydrophobic, any practical utilization of such resins in the chromatography of complex mixtures of structurally similar peptides and proteins would be surprising. Indeed, there is no report which details the operational parameters of these supports in protein purification. However, it is the foregoing two properties of the XAD-type resins which surprisingly make them exceptionally effective for the initial purification stages of highly impure sludge-laden mixtures containing both structurally diverse and structurally similar proteins. One would correctly expect that the large and heterogeneous particle sizes of XAD-type resins would substantially diminish their chromatographic performance due to the slow and unequal dynamics of interaction and, therefore, one would avoid the use of such resins in protein and polypeptide purification. It has been discovered, however, that this seeming deficiency in fact serves as an advantage when applied under precisely defined conditions to highly impure, sludge-laden materials containing growth hormone-like material.

Moreover, of added practical significance in the purification of such growth hormone-like material is the fact that XAD-type resins (1) are readily available at moderate cost, (2) are completely stable throughout the pH range of 1-13, and (3) are amenable to in-column regeneration with aqueous detergents and organic solvents.

The literature does not address, except in a most general manner, the use of XAD-type resins in the purification of proteins and polypeptides. Thus, for example, technical bulletins provided by the Rohm and Haas Company discuss adsorption of proteins on XAD-7 resin but fail to provide any enlightenment regarding the conditions of separation or efficiency of operation. Pietrzyk, D. J. and Stodola, J. D., *Anal. Chem.* 53, 1822–1828 (1981) were the first to analytically examine XAD-4, a co-polymer of polystyrene-divinylbenzene, for utilization with synthetic dipeptides. A further study [Pietrzyk, D. J., Cahill, W. J., and Stodola, J. D., *J. Liquid Chrom.* 5, 443–461 (1982)] with synthetic peptides as large as five residues revealed the possibility of achieving reasonably efficient preparative purification on XAD-4 resin which first had been crushed and sized to significantly smaller particles. Consequently, while these studies did indicate the ability to effectively chromatograph small peptides on macroporous hydrophobic resins, they did not address the question whether mixtures of substantially larger and vastly more complex proteins could be efficiently separated from highly impure mixtures using large particle size supports.

The difficulties of protein purification from highly impure sources have been especially evident with the advent of recombinant DNA technology and its particular suitability to the commercial production of peptides and proteins. Any commercially feasible expression of product by recombinant DNA methodology necessarily carries with it the requirement to isolate the recombinant DNA-sourced product from impurities contained in the originating fermentation broths as well as in the mixtures resulting from subsequent chemical and/or other treatments. The necessity for new commercial-scale protein purification methodology thus has become a high priority item.

An even more complicating factor in the purification of recombinant DNA-sourced proteins arises from the presence in many such proteins of cysteinyl residues. In many cases, following recombinant expression of cysteine-containing proteins, the cysteinyl sulfhydryls are reversibly protected, generally by conversion to S-sulfonates, prior to commencing any protein purification. This conversion treatment and/or other treatments necessarily lead to the production of additional amounts of undesirable sludge-like impurities, in the presence of highly viscous denaturing agents, from which the desired protein must first be separated.

It is essential, therefore, in making processes of this nature commercially feasible, to discover methods that will permit removal of sludge, salt, organic solvents, and other contaminants from the desired product (whether such product is the final product or an intermediate along the way) with little or no loss of such product.

A highly advantageous process which forms the basis of this invention has been discovered for enhancing the purity of gorwth hormone-like material from highly impure stocks thereof obtained via recombinant DNA methods. The process involves subjecting the impure stock to reverse phase purification on a macroporous acrylate ester copolymer resin support.

SUMMARY OF THE INVENTION

Therefore, this invention is directed to a process for separating impurities from an impure mixture containing growth hormone-like material with substantially complete recovery of said growth hormone-like material, which comprises (1) applying said mixture to a reverse phase macroporous acrylate ester copolymer resin support at a pH of from about 7 to about 9; and (2) eluting said growth hormone-like material from said support with an aqueous eluant having a pH of from about 7 to about 9 and containing from about 20% to about 80% by volume of a organic diluent selected from the group consisting of acetone, acetonitrile, and a combination of acetone and acetonitrile.

DETAILED DESCRIPTION OF THE INVENTION

As noted hereinabove, the process of this invention is directed to the purification of highly impure mixtures containing growth hormone-like material. By the term "growth hormone-like material" as used herein is meant (1) growth hormone itself of whatever species, for example, human, bovine, or porcine; (2) precursors to growth insulin, such as reduced (—SH) growth hormone and S-protected growth hormone, for example, growth hormone S-sulfonate; (3) variants of growth hormone or its precursors, for example, structures which have been modified to lengthen and/or shorten the growth hormone amino acid sequence, for example, the 20K variant of human growth hormone, methionyl human growth hormone, and the like; and (4) analogs of growth hormone or its precursors, for example, structures in which the growth hormone amino acid sequence has been modified by replacement of one or more amino acid residues.

The process of this invention involves the use of a macroporous acrylate ester copolymer resin as chromatographic support. Two such supports, highly suited for the purposes of this invention, are available from the Rohm and Haas Company and carry the designation XAD-7 and XAD-8. Of the two, XAD-8 is particularly preferred for the purposes of this invention.

The process of this invention can be divided into three customary chromatographic steps or stages. Only two of these, however, are required. Thus, the process must include a loading and a desorption step, and it may, and preferably does, include an intermediate washing step. Moreover, the process may be carried out in either batch or column mode, although, for the sake of efficiency of purification, it, of course, is much preferred to conduct the process under column conditions. Whether the process of this invention is carried out using the batch or column mode, the particular conditions which are key to its success and which form the basis of the discovery described herein remain constant.

The complex mixture containing growth hormone-like material used in the loading step of this invention generally is obtained as a result of expression by recombinant DNA methodology and may include one or more intervening conversion and/or treatment steps. Customarily, a product is expressed containing an amino acid sequence, at least part of which corresponds to that of growth hormone or a variant or analog thereof. The expression product, if only a portion of it represents growth hormone-like material, will be designed to contain a selective cleavage site to permit growth hormone-like material to be generated chemically or enzymatically from the longer chain expression product. The resulting mixture, as a result of fermentation and cleavage, will contain a wide range of peptides along with an accompanying complex mixture of sludge and other materials and, relatively speaking, only minor amounts of growth hormone-like material.

The mixture may be treated under recognized conditions in the presence of large amounts of urea (generally about 7M) to minimize any peptide aggregation that may tend to occur. The resulting sludge-laden, urea-containing mixture, containing appreciable levels of organic solvents and exhibiting high conductivity, represents the typical material loaded onto the macroporous acrylate ester copolymer in batch or column mode in accordance with the process of this invention.

In carrying out loading of material of the kind described hereinabove, the pH of the sludge-laden, urea-containing mixture is adjusted to a range of from about 7 to about 9, preferably, from about 8 to about 9, and, most preferably, about 8.5, and the resulting solution is brought into contact with the macroporous acrylate ester copolymer resin.

Upon completion of the loading stage, and especially when in the column mode, the resin preferably is washed with an aqueous buffer containing about 10% to about 15% acetone and/or acetonitrile and having a pH of from about 7 to about 9, and, preferably, about 8.5. Any of a wide range of buffering agents can be used, including, for example, Tris, ethylenediamine, and the like. A buffering agent of choice is Tris. The aforementioned aqueous buffer wash may be and preferably is preceded by a urea wash, typically using 7M urea, pH 8.5 50 mM Tris.

Upon completion of loading of the resin, or washing, if such step is included, the growth hormone-like material is eluted from the resin free of sludge and of substantially increased purity and concentration. The mandatory conditions for practical elution of the adsorbed growth hormone-like material are the prescribed pH range and eluant composition. The pH must be in the range of from about 7 to about 9, and, preferably, from about 8 to about 9. The aqueous eluant must contain, on a volume basis, from about 20% to about 80% of acetone, acetonitrile, or a combination of the two. Preferably, the amount of acetone or acetonitrile present in the eluant will be from about 40% to about 50% if elution is carried out isocartically or over a range of from about 20% to about 50% if gradient elution is employed.

The entire process of this invention can be carried out over a wide range of temperatures, for example, anywhere from about 4° C. to about 30° C. Preferably, however, process is conducted at a temperature in the range of from about 4° C. to about 8° C.

The aqueous-organic solution obtained as eluate from the process of this invention contains growth hormone-like material free of contaminating sludge, urea, and salt, and of substantially greater purity when compared with the original mixture as applied to the macroporous acrylate ester copolymer resin. The resulting growth hormone-like material can be recovered from the eluate by routine techniques, or the solution itself can be used in further processing of the material.

One highly useful and wholly unexpected method for treating eluates to separate protein impurities from growth hormone-like materials involves the selective precipitation of such impurities. It has been found that certain protein impurities can be selectively precipitated from eluates containing growth hormone-like material and from about 20% to about 40% acetonitrile by lowering the pH of the eluate to the range from about 5.0 to about 6.5, and, preferably, from about 5.2 to about 5.6. The precipitated impurities are removed by either centrifugation of filtration. Approximately half the total protein in the eluate is found in the precipitate while only about 5% of the growth hormone-like material is present. Thus, the specific activity of the growth hormone-like material in the supernatant fraction following removal of the precipitate is increased by about twofold.

The following examples are provided to illustrate the process of this invention. They are not intended to be limiting on the broad scope thereof.

EXAMPLE 1

Purification of Methionyl Human Growth Hormone

*Escherichia coli* cells containing methionyl human growth hormone produced by recombinant DNA technology were obtained as a moist cell paste by high speed centrifugation of whole cell broth. One kilogram of cell paste was dispersed in 9 liters of cold 7M urea, 50 mM Tris buffer, pH 8.5. Ten ml of toluene and 10 ml of Triton X-100 were added. The pH was adjusted to 8.5, and the volume was adjusted to 10 liters with the urea-Tris buffer. The suspension was agitated with a Tekmar tissue homogenizer at 50% full power over a 48 hour period at 5° C. Several times during the first few hours of extraction, the homogenizer setting was increased to about 90% full power for short periods of about ten minutes each in order to assist in lysis and disruption of the cells.

A one liter (5×52 cm) column of XAD-8 was packed and equilibrated with 7M urea, 50 mM Tris buffer, pH 8.5, in 10% acetonitrile. The feed solution to the column consisted of 4850 ml of cell extract as described above; the extract contained 1.15 grams methionyl human growth hormone in 86.8 grams of total protein (1.32% specific activity). The extract was pumped to the top of the column at a linear flow rate of 13 ml/min. The column was washed with 7M urea, 50mM Tris buffer, pH 8.5, in 10% acetonitrile until the column effluent showed an $O.D._{280nm}$ of 0.12 indicating that most of the non-adsorbed protein had been washed off the column. This step required about 3.3 column volumes or 3300 ml of wash during which cells and cell debris were effectively removed from the column. The wash was changed to 50mM Tris, pH 8.5, in 10% acetonitrile to remove urea; this required about 2 column volumes or 2,000 ml of wash until a negative test for urea was obtained using Azostix test paper.

The methionyl growth hormone was eluted from the column with 40% acetonitrile by volume in 50mM Tris buffer, pH 8.5 at a linear flow rate of about 10 ml/minute. Fractions of the eluate were collected at 2 minute intervals (~20 ml fractions). Elution of methionyl growth hormone from the column was monitored by analytical reversed phase HPLC. Fractions 25 to 60 showed significant amounts of methionyl growth hormone and were pooled (720 ml) and assayed. The pool contained 741 mg methionyl human growth hormone in 2088 mg total protein. The recovery of the methionyl growth hormone from the crude extract was 64% and the specific activity was 35% based on protein, which represents a 27-fold purification from the crude extract or cell lysate. Radioimmunoassay and SDS-polyacrylamide gel electrophoresis confirmed the content of growth hormone in the XAD-8 eluates.

EXAMPLE 2

Purification of 20K Variant of Methionyl Human Growth Hormone.

A moist cell paste was obtained by centrifugation of *E. coli* cells containing the 20K variant of methionyl human growth hormone expressed by recombinant DNA. The cell paste, 587 grams, was dispersed in 4700 ml of 6M guanidine hydrochloride in 0.25M sodium chloride, 0.001M EDTA, pH 9.4. The cell slurry was homogenized using a tissue homogenizer, 0.1% Triton X-100 was added, and the mixture was agitated for 64 hours.

The extract was made 10% v/v with acetonitrile and pumped over a one liter column of XAD-8 (5×50 cm) equilibrated with 10% acetonitrile in 50mM Tris, pH 8.5. The column was washed with about 2.5 liters of 7.5M urea, 50mM Tris, pH 8.5, 10% acetonitrile, until the column effluent became clear and colorless. The column was then washed overnight with about three liters of 50mM Tris, pH 8.5 in 10% acetonitrile.

The column was eluted using a linear gradient containing from 20% to 80% acetonitrile in 50mM Tris, pH 8.5. The flow rate was 12 ml/min., and fractions were collected at two-minute intervals (~24 ml/fraction). The fractions were assayed for 20K methionyl human growth hormone by fast protein liquid chromatography (FPLC), and the fractions containing the growth hormone (fractions 25–65) were pooled and assayed. The pool contained 1.78 grams of the 20K variant in 3.61 grams of total protein. The specific activity of the 20K variant was 49% based on protein.

EXAMPLE 3

Purification of Methionyl Human Growth Hormone from the XAD Eluate by Direct Precipitation of Impurities at pH about 5.5

Glacial acetic acid (~0.2 ml) was added slowly with stirring to 50 ml XAD-8 eluate containing methionyl human growth hormone. The eluate contained about 30% acetonitrile. A flocculent white precipitate formed, and the suspension was allowed to stand at 5° C. for about 1.5 hours. The precipitate was removed by centrifugation and dissolved in 10 ml of distilled water by adjusting the pH to 8.0 with ammonium hydroxide. The solution of the precipitate and the supernatant fraction were assayed, and the results are provided in the Table following.

TABLE

|  | Mg. Protein | Mg. Met-hGH | % Recovery Met-hGH | Specific Activity |
|---|---|---|---|---|
| XAD-8 Eluate | 121 | 33 | 100 | 27% |
| pH 5.5 Supernate | 52.8 | 35.5 | 106 | 67 |
| pH 5.5 Precipitate | 60.0 | 1.0 | 3 | 1.8 |

Balances are not 100% because of handling losses and errors inherent in the assays.

We claim:

1. A process for separating impurities from an impure mixture containing growth hormone-like material with substantially complete recovery of said growth hormone-like material, which comprises:
    (1) applying a complex, impure mixture obtained, without purification, as a result of recombinant DNA expression of a growth hormone-like material to a reverse phase macroporous acrylate ester copolymer resin support at a pH of from about 7 to about 9; and
    (2) eluting said growth hormone-like material from said support with an aqueous eluant having a pH of from about 7 to about 9 and containing from about 20% to about 80% by volume of an organic diluent selected from the group consisting of acetone, acetonitrile, and a combination of acetone and acetonitrile.

2. Process of claim 1, in which the growth hormone-like material has an amino acid sequence which includes that of human growth hormone.

3. Process of claim 1, in which the growth hormone-like material has an amino acid sequence which includes that of bovine growth hormone.

4. Process of claim 1, in which the growth hormone-like material has an amino acid sequence which includes that of the 20K variant of human growth hormone.

5. Process of claim 1, in which the growth hormone-like material is a precursor to growth hormone.

6. Process of claim 1, in which the macroporous acrylate ester copolymer support is XAD-7 or XAD-8.

7. Process of claim 6, in which the macroporous acrylate ester copolymer support is XAD-8.

8. Process of claim 7, in which the impure mixture containing growth hormone-like material is treated under batch conditions.

9. Process of claim 7, in which the impure mixture containing growth hormone-like material is treated under chromatographic column conditions.

10. Process of claim 9, in which the impure mixture containing growth hormone-like material is applied to the macroporous acrylate ester copolymer support at a pH of from about 8 to about 9.

11. Process of claim 9, in which, following application of the impure mixture to the column support and prior to elution, the support is washed with an aqueous buffer having a pH of from about 7 to about 9.

12. Process of claim 9, in which the growth hormone-like material is eluted from the support with an aqueous eluant having a pH of from about 8 to about 9.

13. Process of claim 12, in which the growth hormone-like material is eluted using a gradient eluant that contains a minimum of about 20% and a maximum of about 50% by volume of an organic diluent selected from the group consisting of acetone, acetonitrile, and a combination of acetone and acetonitrile.

14. Process of claim 13, in which the organic diluent is acetone.

15. Process of claim 13, in which the organic diluent is acetonitrile.

16. Process of claim 1, in which the aqueous eluant contains from about 20% to about 40% by volume of acetonitrile, the pH of the eluate obtained from eluting said growth hormone-like material from said support is lowered to the range of from about 5.0 to about 6.5, and the resulting precipitated impurities are removed from the eluate to obtain a solution containing growth hormone-like material of increased purity.

17. Process of claim 16, in which the pH of the eluate is lowered to the range of from about 5.2 to about 5.6.

* * * * *